(12) United States Patent
Wilkinson et al.

(10) Patent No.: US 6,526,363 B2
(45) Date of Patent: Feb. 25, 2003

(54) SYSTEM AND METHOD FOR CALIBRATION AND VERIFICATION OF A SAMPLE ANALYSIS INSTRUMENT

(75) Inventors: James P. Wilkinson, San Diego, CA (US); Henry Eisenson, San Diego, CA (US); Theodore R. Fitzpatrick, Poway, CA (US)

(73) Assignee: Progeny Systems, LLC, San Diego, CA (US)

( * ) Notice: Subject to any disclaimer, the term of this patent is extended or adjusted under 35 U.S.C. 154(b) by 4 days.

(21) Appl. No.: 09/811,325

(22) Filed: Mar. 16, 2001

(65) Prior Publication Data

US 2002/0133306 A1 Sep. 19, 2002

(51) Int. Cl.[7] .................. G01M 19/00; G01N 21/00
(52) U.S. Cl. ............... 702/85; 702/71; 702/124; 250/461.1
(58) Field of Search .................. 702/19, 20, 21, 702/71, 81, 84, 85, 66, 116–117, 124; 250/372, 461.1, 461.2

(56) References Cited

U.S. PATENT DOCUMENTS

| | | | | |
|---|---|---|---|---|
| 5,149,972 A | * | 9/1992 | Fay et al. | 250/461.1 |
| 6,051,603 A | * | 4/2000 | D'Cruz et al. | 514/492 |
| 6,078,681 A | * | 6/2000 | Silver | 382/132 |

* cited by examiner

*Primary Examiner*—Bryan Bui
(74) *Attorney, Agent, or Firm*—Procopio, Cory, Hargreaves & Savitch, LLP

(57) ABSTRACT

A system for calibrating a sperm quality analyzer (SQA) is provided. An optical shutter is inserted into an optical chamber within the SQA. A playback circuit coupled to the optical shutter stores pre-recorded sample waveforms and applies the pre-recorded waveforms to the optical shutter to produce contrast variations in the optical shutter that mimic the random motion of live samples.

36 Claims, 3 Drawing Sheets

SYSTEM AND METHOD FOR CALIBRATION AND VERIFICATION OF A SAMPLE ANALYSIS INSTRUMENT

FIELD OF THE INVENTION

The present invention relates generally to calibration and verification of a measurement instrument and, more particularly, to a system and method for calibrating and verifying a photometric semen quality analyzer.

BACKGROUND OF THE INVENTION

Over the past two decades, most animals have experienced a reduction in overall fertility. This decline in fertility among animals has been attributed to many factors, including pollution and global warming. Subfertility in males can usually be identified by taking a sperm count, which requires magnification to increase the apparent size of the microscopic sperm cells so that they can be quantified by a human or by computer. The microscopic cells are studied to determine the total number of cells per unit of volume, the degree of motility and the general shape of the cells. The overwhelmingly most important fertility measurement, however, is the concentration of motile sperm cells that are capable of impregnating an egg. Prior art techniques for measuring fertility include Computer Assisted Semen Analysis (CASA), general microscopy, biochemical assays and the use of a Sperm Quality Analyzer (SQA).

An SQA is a computerized device used by sperm banks, fertility clinics and laboratories to measure certain characteristics of sperm. During use, a sperm sample is drawn into a transparent capillary with precise internal dimensions. After the sample rises into the capillary, the carrier is inserted into an elongated slot wherein a calibrated light is directed by a fiberoptic conduit to illuminate a small segment of the capillary. A photosensor senses the occurrence and frequency of minute perturbations caused by movement of the sperm cells in the light passing through the capillary. The perturbations are converted into digital data and communicated to a computer, which applies a known algorithm to the data and produces a numerically expressed Sperm Motility Index (SMI) that reflects overall sperm quality or relative fertility of the sperm samples. The SMI is also referred to as the Sperm Quality Index (SQI).

For precise fertility measurements over time, an SQA requires repeated calibration to ensure the fidelity of the fiberoptic conduit. In addition, SQAs are often calibrated against other SQAs in an effort to limit instrument-to-instrument variation. For these reasons, there is a need for a high precision SQA calibration system that utilizes uniform measurement standards in order to reduce instrument-to-instrument variation.

SUMMARY OF THE INVENTION

In one embodiment of the present invention, a system for calibrating a sample analysis instrument is provided. The system comprises an optical shutter that is inserted into an optical chamber within the sample analysis instrument, and a playback circuit coupled to the optical shutter that stores pre-recorded sample waveforms and applies the pre-recorded waveforms to the optical shutter to produce contrast variations in the optical shutter that mimic the random motion of live samples.

In another embodiment of the present invention, a method for calibrating an instrument for analyzing biological samples is provided. The method includes the followings steps:

generating a standard waveform that mimics the known waveform of a particular biological sample;

storing the waveform in a playback circuit; and applying the waveform to an optical shutter that is inserted into the instrument in order to produce contrast variations in the optical shutter that mimic the random motion of live samples.

In a further embodiment of the present invention, a method for calibrating an SQA instrument for analyzing biological samples is provided. The method comprises the following steps:

placing a waveform playback unit, a reference SQA and an SQA to be calibrated adjacent each other;

generating a periodic waveform with the playback unit that is in the bandpass of the input spectrum of the reference SQA;

inserting an optical shutter of the playback unit into an optical chamber of the reference SQ and adjusting the gain of the playback unit until a mid range amplitude is obtained;

transferring the optical shutter from the reference SQA optical chamber to an optical chamber of the SQA to be calibrated;

adjusting baseline lamp intensity DAC values of the SQA to be calibrated to match those of the reference SQA; and storing the adjusted lamp intensity DAC values in a memory in the SQA to be calibrated.

Objects and advantages of the present invention include any of the foregoing, singly or in combination. Further objects and advantages will be apparent to those of ordinary skill in the art, or will be set forth in the following disclosure.

BRIEF DESCRIPTION OF THE DRAWINGS

The present invention is described with reference to the accompanying drawings. In the drawings, like reference numbers indicate identical or functionally similar elements.

DETAILED DESCRIPTION OF PREFERRED EMBODIMENTS

The present invention is directed to an apparatus and method for calibrating and verifying a photometric semen quality analyzer (SQA).

Figure 1:
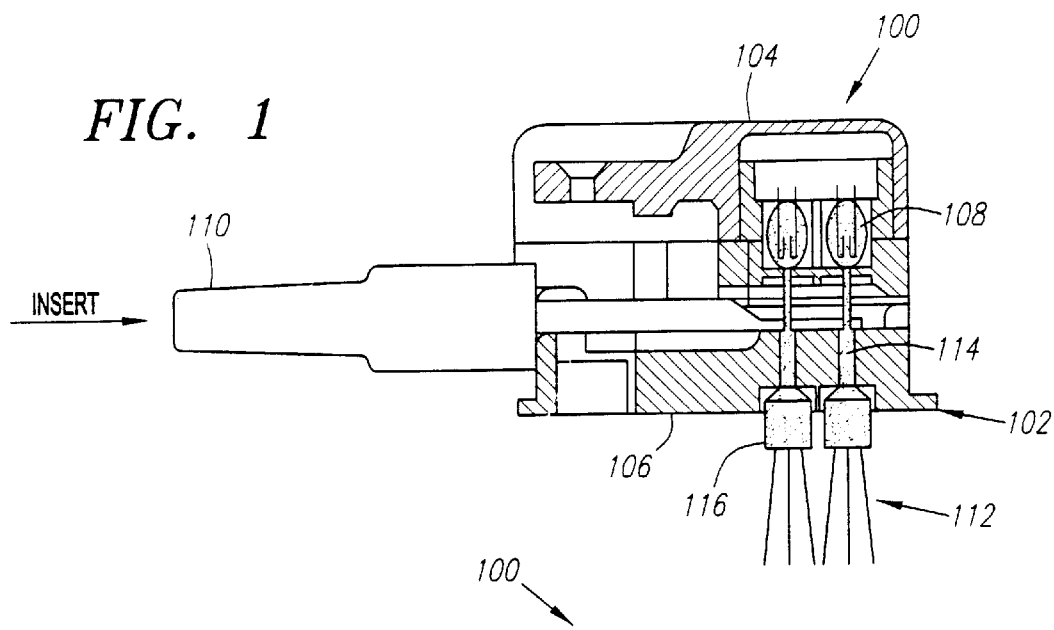
FIG. 1 is a partial sectional view of an optical chamber for semen quality analysis with a capillary containing a live semen sample inserted therein.

FIG. 1 depicts an SQA 100 during normal use. SQA 100 comprises an optical chamber 102 defined by an upper assembly 104 and a lower assembly 106. Upper assembly 104 houses light sources 108 for emitting light that is conveyed through an inserted capillary 110 to optical detectors 112 disposed in lower assembly 106. Optical detectors may comprise fibers 114 that convey the light to phototransistors 116.

During normal use of SQA 100, the operator inserts capillary 110 into optical chamber 102. Capillary 110 houses a specimen to be analyzed, typically a live sperm sample. SQA 100 may include grooves, seats or other alignment mechanisms to insure that the inserted capillary is properly aligned. A computer or controller within SQA 100 then activates light sources 108. From the light passing through the semen sample in capillary 110 and detected by optical detectors 112, the computer can determine the motility of the semen. More detailed information about the normal operation of SQA 100 can be found in International Publication Number WO 99/42577, which is incorporated herein by reference.

Figure 2:
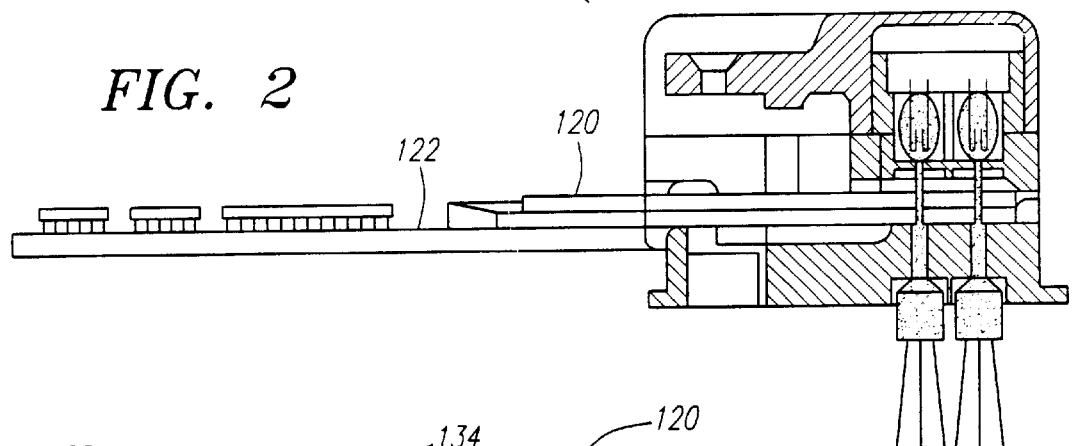
FIG. 2 is a partial sectional view of the optical chamber of FIG. 1 with an optical shutter inserted therein for calibration/testing.

FIG. 2 depicts SQA 100 as configured for calibration and testing in accordance with the present invention. Optical shutter 120 replaces capillary 110 and is electrically connected to playback circuit 122. Shutter 120 is a custom transmissive liquid crystal shutter (LCS) that is contrast modulated by a previously recorded waveform from an SQA instrument that has been deemed a standard. The previously recorded waveform is provided by playback circuit 122. Hence, the same waveform can be played back to any number of instruments so that they may all be calibrated to produce the same results.

Figure 3:
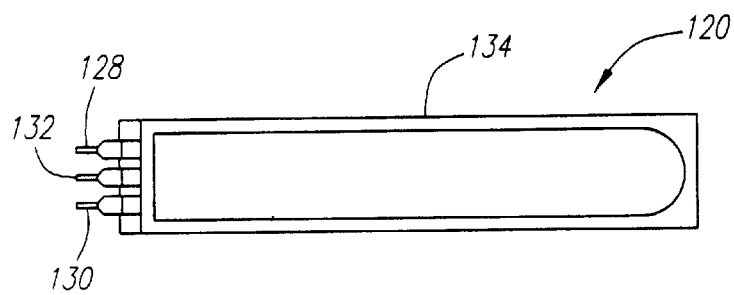
FIG. 3 is a top view of an optical shutter according to the present invention.
Figure 4:
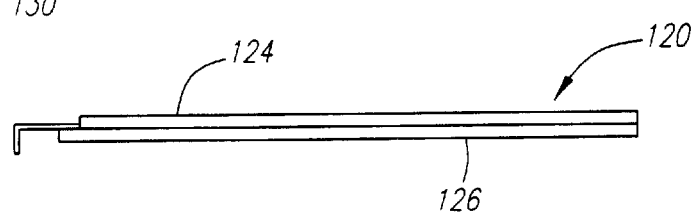
FIG. 4 is a side view of an optical shutter according to the present invention.

Optical shutter 120 is illustrated in more detail in FIGS. 3 and 4. Shutter 120 is of a custom design based on liquid crystal shutter technology. It comprises two glass planes 124 and 126. In one preferred embodiment, the glass planes are approximately 1.25 mm thick by 50 mm long by 10 mm wide. Polarizing layers are applied on both sides of glass planes 124 and 126. A commercial grade film is preferable. If the polarizer used is susceptible to scratching, great care must be taken to ensure that the shutter is not scratched after calibration.

Shutter 120 includes three electrical contacts 128, 130 and 132 for connection to playback circuit 122 and playback of recorded SQA waveforms. In one preferred embodiment, contact 128 is the common plane and contact 130 is the shutter plane. Shutter 120 is of the transmissive type with a positive image. This means that when the voltage applied between the shutter plane and common plane is very small or zero, light will pass through the shutter. When an AC voltage is applied, 180 degrees out of phase between the two planes, shutter 120 darkens thereby reducing the transmission of light.

Shutter 120 also includes a cavity 134 that is filled with a liquid crystal fluid. In one preferred embodiment, the fluid is a twisted nematic, LXD type #16, liquid crystal fluid that offers a very low birefringance and a very good transmission vs. temperature characteristic over the room temperature range. At room temperature, the differential voltage between the planes that causes approximately ten percent of the light to be blocked is 2.2 VACrms, while 3.5 VACrms causes approximately ninety percent of the light to be blocked. Shutter 120 also includes a fill port (not shown) to allow introduction of the liquid crystal fluid into shutter 120.

Figure 5:
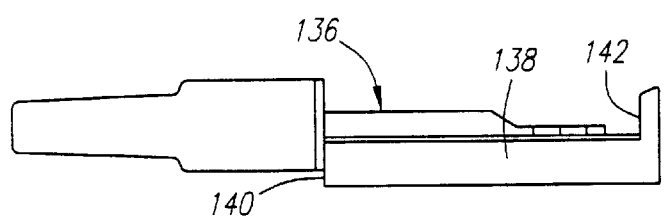
FIG. 5 is a side view of a capillary and optical chamber housing for comparison with FIGS. 3 and 4.

FIG. 5 depicts a capillary 136 and a portion of an optical chamber housing 138. For purposes of comparison, the capillary is scaled to the same scale as shutter 120 in FIGS. 3 and 4. Surface 140 is the reference surface for capillary 136, whereas surface 142 is the reference surface for shutter 120.

Figure 6:
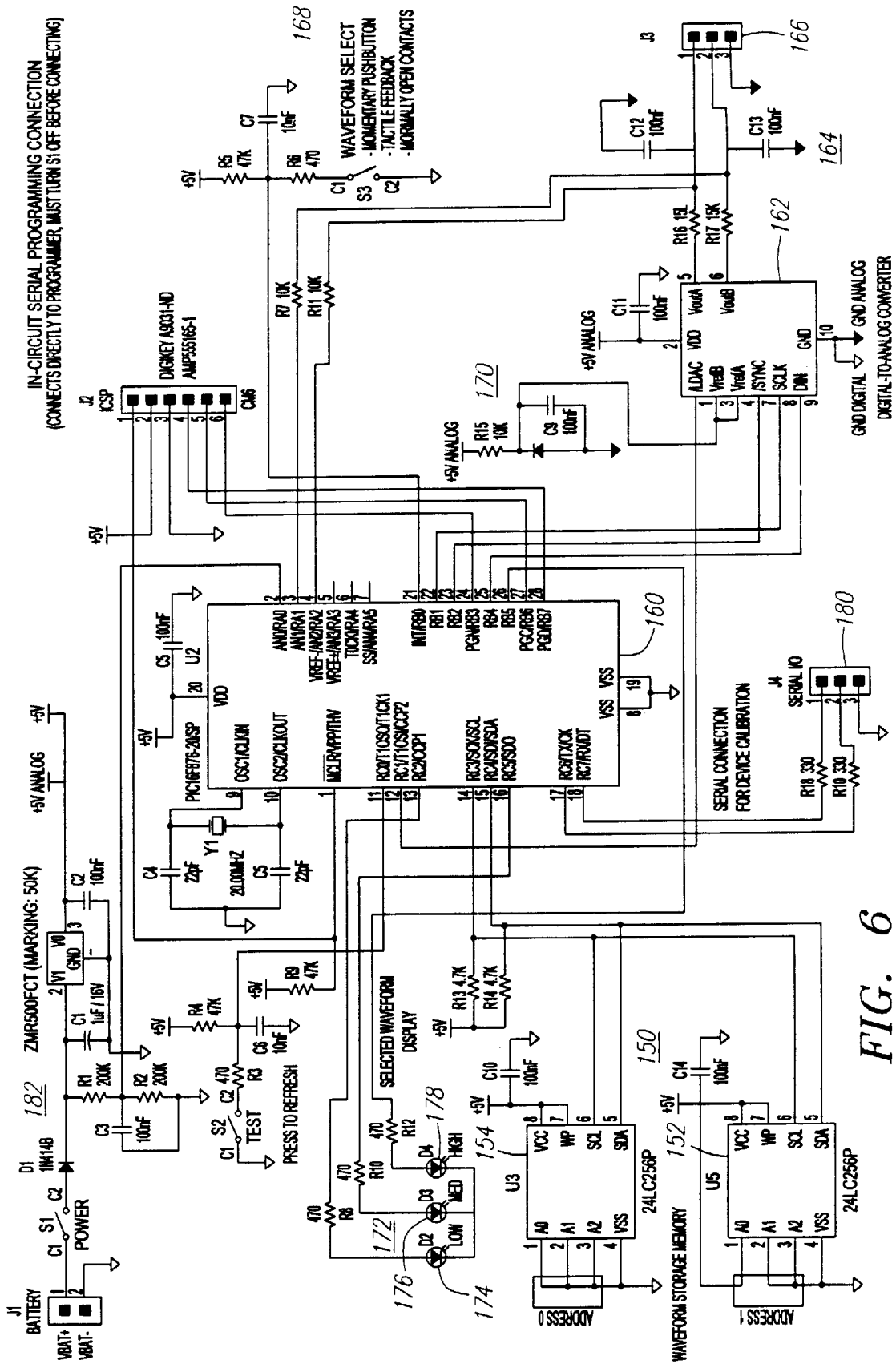
FIG. 6 is a schematic diagram of a playback circuit according to the present invention.

Playback circuit 122 is illustrated in detail in FIG. 6. In brief, circuit 122 stores and plays back previously recorded waveforms that have been deemed "standard". Typically, standard waveforms are acquired from an SQA instrument that has been meticulously calibrated with a laboratory method that uses a large statistical sampling of Makler cell counts performed at various dilutions. In one embodiment, 8000 samples are taken at 400 Hz, using the integers 0 to 1023. Using instrument-embedded digital data acquisition techniques, statistically representative waveforms are recorded at three dilution ratios and labeled "high", "medium" and "low".

The three waveforms are translated into data arrays and stored in waveform storage memory 150. In one embodiment, the waveforms are programmed as an offset plus one byte per sample (0 to 255). In one embodiment, memory 150 comprises serial electrically erasable programmable read only memories (EEPROMs) 152 and 154. In a preferred embodiment, the Microchip 24LC256 EEPROM is used. Serial programming connection 180 is provided to allow programming of the waveforms into memory 150.

Waveform storage memory 150 is coupled to high-speed microcontroller 160, which is powered by power supply circuit 182. In one embodiment, the microcontroller is a PIC16F876. Any of the three waveforms stored in memory 150 can be played back via microcontroller 160 to a digital-to-analog converter (DAC) 162 that is coupled to microcontroller 160. Waveform selector 168 is coupled to microcontroller 160 and permits the operator to select any one of the three stored waveforms. In one embodiment, waveform selector 168 is a momentary pushbutton with tactile feedback and normally open contacts.

Waveform display 172 is coupled to microcontroller 160 to display the selected waveform. In the illustrated embodiment, display 172 comprises three light emitting diodes 174, 176 and 178. LED 174 is illuminated when the "low" waveform is selected, LED 176 is illuminated when the "medium" waveform is selected, and LED 178 is illuminated when the "high" waveform is selected. Alternatively, display 172 may comprise a single LED that signals which waveform has been selected by blinking. For example, one blink may indicate the "low" waveform, two blinks may indicate the "medium" waveform and three blinks may indicate the "high" waveform.

DAC 162 is preferably a two-channel, 12-bit DAC. The two DAC channels are driven by a single waveform at precise gain and offset, 180 degrees out of phase from each other. Reference voltage source 170 is coupled to DAC 162 to help maintain system accuracy over small variations in supply voltage and system temperature. The output of DAC 162 is a differential AC waveform chopped at approximately 60 to 100 Hz, with the sperm signal (rolled off at approximately 15.5 Hz) modulated on top of it.

The output waveform is applied to opposing planes of shutter 120 via connector 166. De-glitching filter 164 is interposed between DAC 162 and shutter 120 in order to remove small DAC switching transients. In one embodiment, de-glitching filter 164 has a 3-dB point of approximately 100 Hz. The waveform applied to shutter 120 is preferably centered in the linear portion of the liquid crystal shutter "contrast vs. applied voltage" curve. The result is application of a repeatable, digitally derived stimulus to shutter 120 where normally the biological stimulus (i.e. live semen samples) would be present. The recorded waveform produces contrast variations in the liquid crystal shutter that mimic the random motion of live cells. Where live sperm cause intensity variations in photodetector 112 by blocking, passing and scattering light, liquid crystal shutter 120 causes almost identical intensity variations by virtue of its waveform modulated contrast. Detector 112 sees intensity variations of the beam fed to it through the fiber. The intensity variations correspond directly to contrast variations. A darker contrast produces a lower intensity and a lighter contrast produces a higher intensity.

SQA 100 processes the analog signal generated by photodetector 112 by AC coupling the signal to a gain stage. In one embodiment, the gain is 101. The signal is offset by 2.5 volts and fed into a 2-pole lowpass Salen-Key filter with a cutoff frequency of 15.5 Hz and Q of 0.729. This signal is fed to an analog-to-digital (ADC) converter and run through a real-time algorithm that discriminates peaks in the signal. Activity counts are accumulated using a thresholding technique on alternating peaks. These activity counts are fed into a look-up table that converts activity counts to Sperm Quality Index (SQI) units. The primary purpose of the look-up table is to linearize the response. The SQI value is then displayed on the screen to the user. Since the standard waveform that was fed to SQA 100 has a known SQI, SQA 100 is then calibrated to closely match the SQI of the standard waveform.

Importantly, the waveform can be played back to any number of instruments so that they may all be calibrated to produce the same results. This calibration method keeps instrument-to-instrument variation to a minimum. Running a test with the optical shutter in place gives the user confidence that an SQA instrument is working properly when unexpected results are obtained from live samples.

An alternative method of calibration is illustrated in FIGS. 7a–7d. In the present context, "precision" is defined as the closeness of the measured SQI value to the intended value. On the other hand, "accuracy" relates to instrument-to-instrument variation. The precision of an SQA instrument can be preserved in one or more "gold standard" or reference instruments. The alternative method of calibration entails transferring the calibration of a gold standard or reference SQA instrument via periodic waveforms to other SQA instruments to reduce calibration errors that may be introduced due to the random nature of recorded waveforms.

The alternate calibration method uses a periodic waveform with a controlled amplitude rather than a random biological waveform. The goal is to transfer the net lamp intensity calibration from the gold standard SQA to the SQA under calibration. By using net lamp intensity calibration, variables such as temperature, component tolerances and manufacturing tolerances are nullified.

Figure 7A:
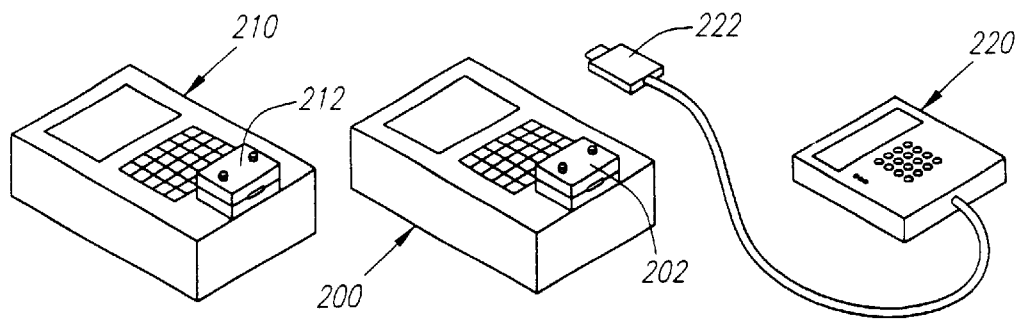
FIGS. 7*a*–7*d* illustrate an alternate method of SQA calibration according to the present invention.
Figure 7B:
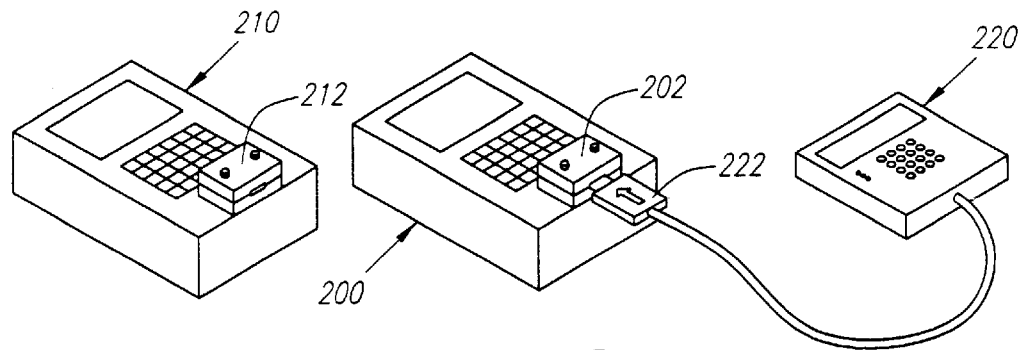
Figure 7C:
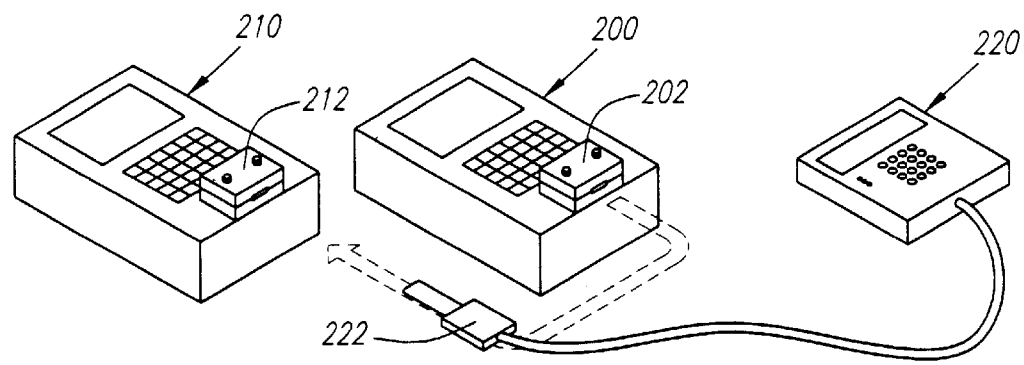

FIGS. 7a–7b illustrate a reference or "gold standard" SQA 200, an SQA to be calibrated 210 and a waveform storage and playback unit 220. Unit 220, in one embodiment, houses a waveform playback circuit such as circuit 122 illustrated in FIG. 6 and described above. The method of calibration illustrated in FIGS. 7a–7b comprises the following steps:

1. Waveform playback unit 220, reference SQA 200 and the SQA 210 under calibration are placed proximate each other on a workbench or other surface or area and allowed to thermally stabilize to the ambient room temperature (~65 F. to 75 F.). The exact temperature is not as important as the fact that the two SQA instruments and the playback unit are at the same temperature.

2. Both SQAs 200, 210 are configured in a factory mode that digitally sends conditioned data signals to a PC connected to the SQAs (not shown). Waveforms from the SQAs can be viewed graphically and numerically analyzed in real time on the PC. As an alternative to real time calibration, the waveforms can be recorded to disk and programmatically compared to the waveforms recorded in step 4 below.

3. Playback unit 220 is used to produce a periodic waveform in the bandpass of the input spectrum of the SQAs. In one embodiment, the frequency of this periodic waveform can range from approximately 3 to 10 Hz.

4. Playback unit 220 includes an optical shutter 222 for playback of recorded waveforms. Shutter 222 may take the form of shutter 120 described with reference to FIGS. 3 and 4. Shutter 222 is inserted into optical chamber 202 of reference SQA 200 (FIG. 7b) and the gain is adjusted until a mid range amplitude is observed in the displayed waveform on the PC connected to SQA 200. This mid range amplitude is used as a standard calibration level in subsequent calibrations. A real-time peak detector displays the peak-to-peak amplitudes for two signal channels in A/D units (see description of playback circuit 122 above), which are recorded by a technician when the mid-range waveform stabilizes. A short (~10–20 sec) segment of the waveform is also recorded at this point. Through the use of appropriate software or hardware, the peak detector input may be additionally filtered.

Figure 7D:
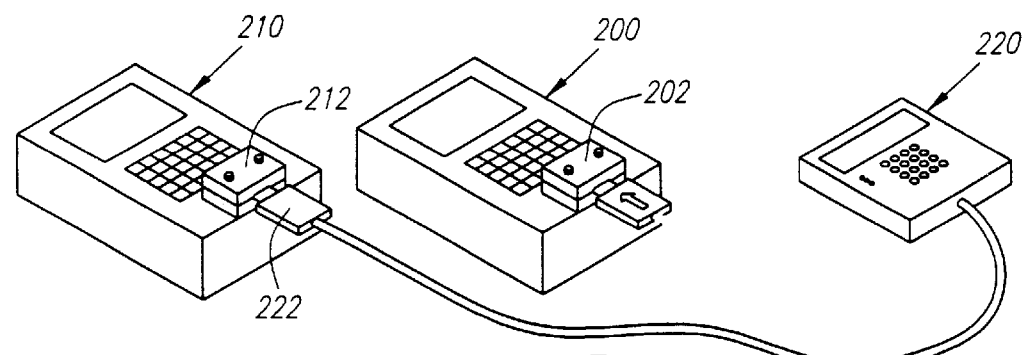

5. Shutter 222 is then removed from the reference SQA optical chamber 202 (FIG. 7c) and inserted into optical chamber 212 of the SQA 210 to be calibrated (FIG. 7d).

6. The baseline lamp intensity DAC values of SQA 210 are adjusted (without changing any parameters for each of the two signal channels) to match the peak-to-peak A/D amplitudes recorded for the two channels in step 4. The lamps are incrementally adjusted until the calibration criteria are satisfied (i.e. the peak-to-peak values displayed for SQA 210 match the peak-to-peak values of reference SQA 200.

7. The matching lamp intensity DAC values are stored in a storage memory, such as an EEPROM, in SQA 210, thereby successfully transferring the net lamp intensity calibration of reference SQA has been successfully transferred to the SQA under calibration.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A system for calibrating a sample analysis instrument comprising:
    an optical shutter that is inserted into an optical chamber within the sample analysis instrument; and
    a playback circuit electrically coupled to the optical shutter that stores pre-recorded sample waveforms and applies one of the pre-recorded waveforms having a known characteristic to the optical shutter to produce contrast variations in the optical shutter that mimic the random motion of live samples, the instrument measuring a characteristic of the applied waveform from the contrast variations, and the instrument being calibrated by adjusting the measured characteristic to match the known characteristic.

2. A system as claimed in claim 1, wherein the samples are live semen samples.

3. A system as claimed in claim 1, wherein the optical shutter comprises two glass planes with electrical contacts for coupling the shutter to the playback circuit.

4. A system as claimed in claim 3, wherein the two glass planes have polarizing layers applied on both sides.

5. A system as claimed in claim 1, wherein the optical shutter includes three electrical contacts for connection to the playback circuit and playback of recorded waveforms.

6. A system as claimed in claim 1, wherein the playback circuit comprises:

a microcontroller;

a waveform storage memory coupled to the microcontroller for storing the pre-recorded waveforms; and a digital-to-analog converter coupled to the microcontroller for producing an analog waveform to be output to the optical shutter.

7. A system as claimed in claim 6, wherein the waveform storage memory comprises at least one electrically erasable programmable read only memory.

8. A system as claimed in claim 6, wherein the waveforms are recorded at dilution ratios of low, medium and high.

9. A system as claimed in claim 8, further comprising a waveform selector coupled to the microcontroller.

10. A system as claimed in claim 9, wherein the waveform selector permits selection of any of the three stored waveforms.

11. A system as claimed in claim 10, further comprising a waveform display coupled to the microcontroller.

12. A system as claimed in claim 11, wherein the waveform display comprises three light emitting diodes that indicate the selected waveform when illuminated.

13. A system as claimed in claim 11, wherein the waveform display comprises a single light emitting diode that indicates the selected waveform by blinking.

14. A system as claimed in claim 6, wherein the digital-to-analog converter is a two-channel converter driven by a single waveform at precise gain and offset, the two channels driven 180 degrees out of phase from each other.

15. A system as claimed in claim 1, wherein the known and measured characteristics represent a sperm quality index.

16. A method for calibrating an instrument for analyzing biological samples comprising:

generating a standard waveform that mimics a known waveform having a known characteristic of a particular biological sample;

storing the waveform in a playback circuit;

applying the waveform to an optical shutter that is inserted into the instrument in order to produce contrast variations in the optical shutter that mimic the random motion of live samples;

measuring a characteristic of the applied waveform from the contrast variations; and calibrating the instrument by adjusting the measured characteristic to match the known characteristic.

17. A method as claimed in claim 16, wherein the samples are live semen samples.

18. A method as claimed in claim 16, wherein the optical shutter comprises two glass planes with electrical contacts for coupling the shutter to the playback circuit.

19. A method as claimed in claim 18, wherein the two glass planes have polarizing layers applied on both sides.

20. A method as claimed in claim 16, wherein the liquid crystal shutter includes three electrical contacts for connection to the playback circuit and playback of recorded waveforms.

21. A method as claimed in claim 16, wherein the playback circuit comprises:

a microcontroller;

a waveform storage memory coupled to the microcontroller for storing the pre-recorded waveforms; and a digital-to-analog converter coupled to the microcontroller for producing an analog waveform to be output to the optical shutter.

22. A method as claimed in claim 21, wherein the waveform storage memory comprises at least one electrically erasable programmable read only memory.

23. A method as claimed in claim 21, wherein the waveforms are recorded at dilution ratios of low, medium and high.

24. A method as claimed in claim 23, further comprising a waveform selector coupled to the microcontroller.

25. A method as claimed in claim 24, wherein the waveform selector permits selection of any of the three stored waveforms.

26. A method as claimed in claim 25, further comprising a waveform display coupled to the microcontroller.

27. A method as claimed in claim 26, wherein the waveform display comprises three light emitting diodes that indicate the selected waveform when illuminated.

28. A method as claimed in claim 26, wherein the waveform display comprises a single light emitting diode that indicates the selected waveform by blinking.

29. A method as claimed in claim 21, wherein the digital-to-analog converter is a two-channel converter driven by a single waveform at precise gain and offset, the two channels driven 180 degrees out of phase from each other.

30. A method as claimed in claim 29, wherein a reference voltage is coupled to the digital-to-analog converter to maintain system accuracy.

31. A method for calibrating an SQA instrument for analyzing biological samples comprising:

placing a waveform playback unit having an optical shutter, a reference SQA having an optical chamber and an SQA to be calibrated and having an optical chamber adjacent each other;

generating a periodic waveform with the playback unit that is in the bandpass of the input spectrum of the reference SQA;

inserting the optical shutter of the playback unit into the optical chamber of the reference SQA and adjusting the gain of the playback unit until a mid range amplitude is obtained;

transferring the optical shutter from the reference SQA optical chamber to the optical chamber of the SQA to be calibrated;

adjusting baseline lamp intensity DAC values of the SQA to be calibrated to match those of the reference SQA; and storing the adjusted lamp intensity DAC values in a memory in the SQA to be calibrated.

32. A method as claimed in claim 31, further comprising the step of allowing the playback unit, the reference SQA and the SQA to be calibrated to thermally stabilize to an ambient temperature.

33. A method as claimed in claim 31, further comprising the step of configuring the SQAs to send conditioned data signals to a PC such that the waveforms can be viewed graphically and numerically analyzed in real time.

34. A method as claimed in claim 31, wherein the frequency of the periodic waveform ranges from approximately three Hz to approximately ten Hz.

35. A method as claimed in claim 31, wherein the mid range amplitude is a standard calibration level that is used in subsequent calibrations.

36. A method as claimed in claim 31, wherein the baseline lamp intensity DAC values of the SQA to be calibrated are incrementally adjusted until its peak-to-peak values match the peak-to-peak values of the reference SQA.

* * * * *